(12) United States Patent
Craig et al.

(10) Patent No.: US 11,529,038 B2
(45) Date of Patent: Dec. 20, 2022

(54) ENDOSCOPE WITH INERTIAL MEASUREMENT UNITS AND / OR HAPTIC INPUT CONTROLS

(71) Applicant: CONVERGASCENT LLC, Minneapolis, MN (US)

(72) Inventors: Brian H. Craig, Minneapolis, MN (US); Dwight Meglan, Minneapolis, MN (US)

(73) Assignee: ELEMENTS ENDOSCOPY, INC., Minneapolis, MN (US)

( * ) Notice: Subject to any disclaimer, the term of this patent is extended or adjusted under 35 U.S.C. 154(b) by 265 days.

(21) Appl. No.: 16/586,732

(22) Filed: Sep. 27, 2019

(65) Prior Publication Data

US 2020/0100647 A1 Apr. 2, 2020

Related U.S. Application Data

(60) Provisional application No. 62/740,314, filed on Oct. 2, 2018.

(51) Int. Cl.
*A61B 1/00* (2006.01)
*A61B 1/005* (2006.01)
*A61B 1/01* (2006.01)

(52) U.S. Cl.
CPC ........ *A61B 1/00006* (2013.01); *A61B 1/0005* (2013.01); *A61B 1/00009* (2013.01); *A61B 1/00039* (2013.01); *A61B 1/00045* (2013.01); *A61B 1/0052* (2013.01); *A61B 1/00057* (2013.01); *A61B 1/0057* (2013.01); *A61B 1/00124* (2013.01); *A61B 1/01* (2013.01)

(58) Field of Classification Search
CPC ............ A61B 1/00006; A61B 1/00039; A61B 1/00045; A61B 1/0005; A61B 1/00057; A61B 1/00124; A61B 1/0057
See application file for complete search history.

(56) References Cited

U.S. PATENT DOCUMENTS

| | | | |
|---|---|---|---|
| 4,911,148 A | 3/1990 | Sosnowski et al. | |
| 4,919,112 A | 4/1990 | Siegmund | |

(Continued)

FOREIGN PATENT DOCUMENTS

| | | |
|---|---|---|
| CN | 103251455 B | 4/2016 |
| WO | 2016209769 A1 | 12/2016 |
| WO | 2017096388 A2 | 6/2017 |
| WO | 2018005928 A1 | 1/2018 |

OTHER PUBLICATIONS

International Search Report and Written Opinion in corresponding international application PCT/US2019/053658 dated Feb. 12, 2020.

(Continued)

*Primary Examiner* — John P Leubecker
*Assistant Examiner* — Jae Woo
(74) *Attorney, Agent, or Firm* — Medler Ferro Woodhouse & Mills PLLC (57) ABSTRACT

An endoscope having an insertion tube with a distal optical module and a releasable handle. In a semi-robotic embodiment, the handle comprises haptic controllers and a computer configured for steering and/or adjusting physical properties of the insertion tube in response to one or more command inputs from the haptic controllers. The computer may also convert image data received from the optical module into two-dimensional images displayable on a monitor. The endoscope may have inertial measurement units (IMUs) for providing data to the computer for creating a digital three-dimensional image representation of an anatomy model and/or for facilitating handling properties of the endoscope.

22 Claims, 4 Drawing Sheets

(56) References Cited

U.S. PATENT DOCUMENTS

| | | | |
|---|---|---|---|
| 6,672,338 B1* | 1/2004 | Esashi | A61M 25/0158 138/119 |
| 6,817,973 B2 | 11/2004 | Merril et al. | |
| 7,815,436 B2* | 10/2010 | Cunningham | G09B 23/285 345/158 |
| 8,096,943 B2 | 1/2012 | Melville | |
| 8,409,080 B2* | 4/2013 | Gumbs | A61B 1/0016 600/152 |
| 8,827,948 B2* | 9/2014 | Romo | A61B 6/4423 604/95.04 |
| 8,888,688 B2 | 11/2014 | Julian et al. | |
| 9,107,573 B2 | 8/2015 | Birnkrant | |
| 9,119,655 B2* | 9/2015 | Bowling | A61B 34/10 |
| 9,220,398 B2 | 12/2015 | Woodley et al. | |
| 9,422,139 B1 | 8/2016 | Bialkowski et al. | |
| 9,855,108 B2* | 1/2018 | Yeung | A61B 34/30 |
| 10,013,082 B2* | 7/2018 | Schecter | G16H 40/63 |
| 10,143,360 B2* | 12/2018 | Roelle | A61B 34/30 |
| 10,154,239 B2* | 12/2018 | Casas | G06F 3/011 |
| 10,159,536 B2* | 12/2018 | Kralicky | A61B 90/03 |
| 10,168,356 B2* | 1/2019 | Campbell | G01R 1/06788 |
| 10,244,926 B2* | 4/2019 | Noonan | A61B 1/051 |
| 10,485,409 B2* | 11/2019 | Di Natali | A61B 1/041 |
| 10,722,319 B2* | 7/2020 | Farritor | A61B 90/50 |
| 10,898,275 B2* | 1/2021 | Ye | A61B 1/2676 |
| 10,948,297 B2* | 3/2021 | Derhy | G06V 20/56 |
| 11,013,564 B2* | 5/2021 | Palmowski | A61B 34/30 |
| 11,122,965 B2* | 9/2021 | Valdastri | A61B 1/018 |
| 2001/0016804 A1* | 8/2001 | Cunningham | G09B 23/285 703/7 |
| 2002/0080248 A1* | 6/2002 | Adair | A61B 1/00096 348/308 |
| 2003/0164952 A1* | 9/2003 | Deichmann | G01B 11/24 356/603 |
| 2004/0263474 A1 | 12/2004 | Gregorio et al. | |
| 2005/0075538 A1* | 4/2005 | Banik | A61B 1/0008 600/152 |
| 2005/0131279 A1* | 6/2005 | Boulais | A61B 1/0684 600/141 |
| 2005/0177287 A1* | 8/2005 | Wang | B60K 37/06 700/83 |
| 2005/0182518 A1* | 8/2005 | Karlsson | G05D 1/0246 700/253 |
| 2006/0106281 A1* | 5/2006 | Boulais | A61B 1/00059 600/101 |
| 2007/0032723 A1* | 2/2007 | Glossop | A61B 18/18 600/424 |
| 2007/0129604 A1 | 6/2007 | Hatcher et al. | |
| 2007/0286764 A1* | 12/2007 | Noguchi | A61B 1/123 422/62 |
| 2008/0015558 A1* | 1/2008 | Harlan | A61B 1/0011 606/15 |
| 2008/0027278 A1* | 1/2008 | Mizuno | A61B 1/0684 600/109 |
| 2008/0214896 A1 | 9/2008 | Krupa et al. | |
| 2008/0262312 A1* | 10/2008 | Carroll | A61B 1/07 600/160 |
| 2008/0312501 A1* | 12/2008 | Hasegawa | A61B 1/0005 600/117 |
| 2009/0135249 A1* | 5/2009 | Hirakawa | G16H 10/60 348/74 |
| 2009/0225320 A1* | 9/2009 | Bendall | A61B 1/07 356/447 |
| 2009/0326714 A1* | 12/2009 | Buckingham | B25J 13/089 700/258 |
| 2010/0160728 A1* | 6/2010 | Yoshie | A61B 34/76 600/117 |
| 2010/0280365 A1* | 11/2010 | Higgins | G06V 10/754 382/128 |
| 2010/0331820 A1* | 12/2010 | Prisco | A61B 1/0016 604/528 |
| 2011/0009863 A1 | 1/2011 | Marczyk et al. | |
| 2011/0112361 A1* | 5/2011 | Ishigami | A61B 1/00052 600/109 |
| 2011/0251519 A1* | 10/2011 | Romoscanu | A61M 25/0053 600/585 |
| 2012/0010506 A1* | 1/2012 | Ullrich | A61B 8/12 600/440 |
| 2012/0071752 A1* | 3/2012 | Sewell | A61B 8/12 345/650 |
| 2012/0100729 A1* | 4/2012 | Edidin | H01R 13/622 439/38 |
| 2013/0023917 A1 | 1/2013 | Cruz Hernandez et al. | |
| 2014/0024891 A1* | 1/2014 | Motoki | A61B 1/00045 600/103 |
| 2014/0031626 A1* | 1/2014 | Schwarz | A61B 1/00117 600/149 |
| 2014/0243660 A1* | 8/2014 | Klinder | A61B 5/065 600/424 |
| 2014/0296633 A1* | 10/2014 | Gumbs | A61B 1/00133 600/109 |
| 2015/0011830 A1* | 1/2015 | Hunter | A61B 1/0055 600/118 |
| 2015/0018622 A1* | 1/2015 | Tesar | A61B 1/05 600/202 |
| 2015/0223725 A1* | 8/2015 | Engel | A61B 1/00006 600/417 |
| 2015/0289946 A1* | 10/2015 | Johansson | G09B 23/285 434/262 |
| 2015/0293592 A1* | 10/2015 | Cheong | G06F 1/163 345/173 |
| 2016/0001038 A1 | 1/2016 | Romo et al. | |
| 2016/0022125 A1* | 1/2016 | Nicolau | A61B 34/20 600/109 |
| 2016/0191887 A1* | 6/2016 | Casas | G06T 19/006 348/47 |
| 2016/0256230 A1 | 9/2016 | Kowshik et al. | |
| 2016/0287346 A1 | 10/2016 | Hyodo et al. | |
| 2016/0361819 A1 | 12/2016 | Wakai et al. | |
| 2017/0035526 A1* | 2/2017 | Farritor | A61B 34/35 |
| 2017/0049298 A1* | 2/2017 | Hunter | A61B 1/0052 |
| 2017/0105609 A1* | 4/2017 | Nakayama | A61B 1/00172 |
| 2017/0181808 A1* | 6/2017 | Panescu | A61B 34/30 |
| 2017/0273542 A1* | 9/2017 | Au | A61B 1/00006 |
| 2017/0354470 A1* | 12/2017 | Farritor | A61B 17/02 |
| 2018/0028049 A1* | 2/2018 | Takahashi | A61B 1/0056 |
| 2018/0028271 A1 | 2/2018 | Rockrohr | |
| 2018/0049622 A1* | 2/2018 | Ryan | A61B 34/10 |
| 2018/0177390 A1* | 6/2018 | Iannitti | A61B 1/00045 |
| 2018/0184892 A1* | 7/2018 | Truckai | A61M 31/00 |
| 2018/0279852 A1* | 10/2018 | Rafii-Tari | A61B 5/0816 |
| 2018/0296075 A1* | 10/2018 | Meglan | A61B 1/05 |
| 2018/0296281 A1* | 10/2018 | Yeung | G06N 3/0454 |
| 2018/0368664 A1* | 12/2018 | Nagda | A61B 1/0051 |
| 2019/0000568 A1* | 1/2019 | Connolly | A61B 90/90 |
| 2019/0000578 A1* | 1/2019 | Yu | A61B 34/10 |
| 2019/0005838 A1* | 1/2019 | Yu | G06F 3/014 |
| 2019/0005848 A1* | 1/2019 | Garcia Kilroy | A61B 34/10 |
| 2019/0015012 A1* | 1/2019 | Raudins | A61B 90/361 |
| 2019/0031235 A1* | 1/2019 | Lee | B62D 5/006 |
| 2019/0053691 A1* | 2/2019 | Hansen | A61B 17/29 |
| 2019/0226852 A1* | 7/2019 | Xie | G01C 21/20 |
| 2019/0231220 A1* | 8/2019 | Refai | H04N 5/22541 |
| 2019/0380781 A1* | 12/2019 | Tsai | G06V 10/76 |
| 2019/0380787 A1* | 12/2019 | Ye | A61B 1/0016 |
| 2020/0053335 A1* | 2/2020 | Casas | H04N 13/296 |
| 2020/0129046 A1* | 4/2020 | Sinay | A61B 1/00071 |
| 2020/0187898 A1* | 6/2020 | Toporek | A61B 8/483 |
| 2020/0302510 A1* | 9/2020 | Chachek | G06K 9/6289 |
| 2020/0359997 A1* | 11/2020 | Caswell | A61B 1/0057 |
| 2021/0153723 A1* | 5/2021 | Yip | A61B 1/00156 |
| 2021/0298795 A1* | 9/2021 | Bowling | B25J 9/1671 |

OTHER PUBLICATIONS

Endoscopic Orientation Correction, Medical Image Computing and Computer-Assisted Intervention—MICCAI 2009: 12th International Conference, London, UK, Sep. 20-24, 2009, Proceedings, Part I (pp. 459-466).

(56) References Cited

OTHER PUBLICATIONS

Intuitive User Interfaces Increase Efficiency in Endoscope Tip Control, Surgical Endoscopy, 2014, DOI 10.1007/s00464-014-3510-1.
Feasibility of Joystick Guided Colonoscopy, Journal of Robotic Surgery, 2015; 9(3) (pp. 173-178).

* cited by examiner

ENDOSCOPE WITH INERTIAL MEASUREMENT UNITS AND / OR HAPTIC INPUT CONTROLS

CROSS-REFERENCE TO RELATED APPLICATION(S)

The present application claims priority to U.S. Provisional Patent Application No. 62/740,314, titled "FLEXIBLE ENDOSCOPE WITH INERTIAL MEASUREMENT UNITS," filed Oct. 2, 2018, the disclosure of which is hereby incorporated by reference in its entirety.

TECHNICAL FIELD

The present disclosure relates generally to endoscopes and associated systems and methods.

BACKGROUND

An endoscope is an illuminated optical, typically slender and tubular instrument used to look deep into the body. A flexible endoscope has a flexible insertion tube with a distal segment that can be controllably deflected by tensioning control cables to navigate the sometimes-tortuous pathways through the body. An endoscope may be designed for use in particular diagnostic or therapeutic endoscopy procedures, and is named accordingly, for example gastrointestinal endoscope, duodenoscope, bronchoscope, cystoscope, ureteroscope, or hysteroscope.

DETAILED DESCRIPTION

The present disclosure relates generally to endoscopes and associated systems and methods. Specific details of several embodiments of the present technology are described herein with reference to FIGS. 1-4. Although many of the embodiments are described with respect to endoscope devices, systems, and methods, other embodiments in addition to those described herein are within the scope of the present technology. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the terms "distal" and "proximal" define a position or direction with respect to a clinician or a clinician's control device (e.g., a handle of an endoscope). The terms, "distal" and "distally" refer to a position distant from or in a direction away from a clinician or a clinician's control device along the length of device. The terms "proximal" and "proximally" refer to a position near or in a direction toward a clinician or a clinician's control device along the length of device. The headings provided herein are for convenience only and should not be construed as limiting the subject matter disclosed.

As shown in FIGS. 1-4, an endoscope system 10 includes a flexible endoscope 15, a computer 16, and a monitor 17. Monitor 17 is located separately from or extrinsic to endoscope 15 and communication therebetween may be wireless (e.g. WLAN, WPAN radio networks) or via an electrical cable or data port 18 as indicated by broken lines in FIG. 1. Endoscope 15 includes an elongate assembly having a distal region configured for insertion into a living body, the entire assembly referred to herein as a flexible elongate insertion tube 20.

An optical module 22 is disposed at distal end 21 of insertion tube 20 and is adapted to receive images of an interior of a hollow organ or other targeted cavity of a living body. Optical module 22 can be selected from various configurations, none of which is shown. In a first configuration, optical module 22 comprises an outer casing, a lens or lens assembly, a PCB containing a camera chip and a connector that may be directly mounted on the PCB or attached to the PCB via a flexible electrical cable. In this configuration, an illumination source is separate from the optical module and must be integrated elsewhere into the endoscope body. In a second configuration, optical module 22 comprises an outer casing, a lens or lens assembly, an LED lighting system, a PCB containing a camera chip and a connector that may be directly mounted on the PCB or attached to the PCB via a flexible electrical cable. Alternatively, more than one optical module 22 may be mounted at distal end 21 of insertion tube 20.

Figure 2:
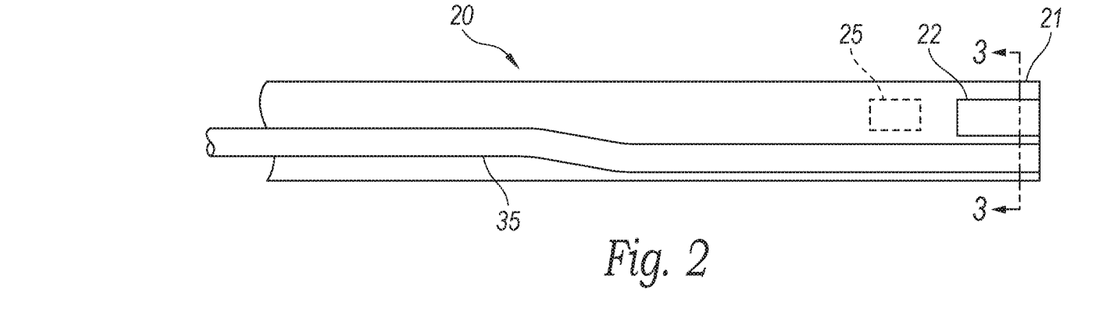
FIG. 2 shows a longitudinal cross-sectional and partially schematic view of a distal portion of an endoscope in accordance with embodiments of the present technology.
Figure 5:
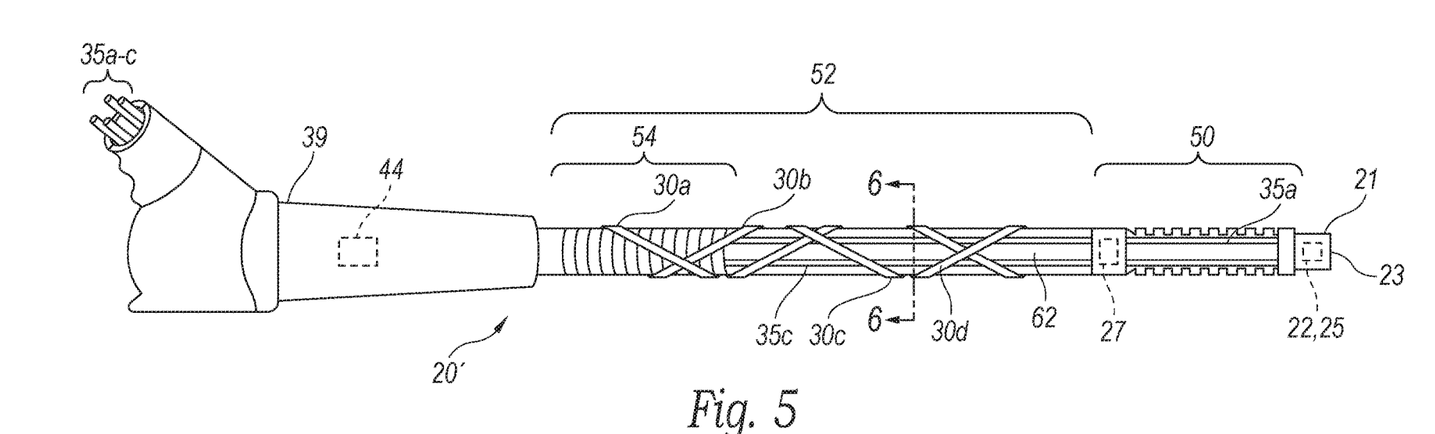
FIG. 5 is a side view of an insertion tube in accordance with another embodiment of the present technology. The outer sheath is omitted for clarity.
Figure 6:
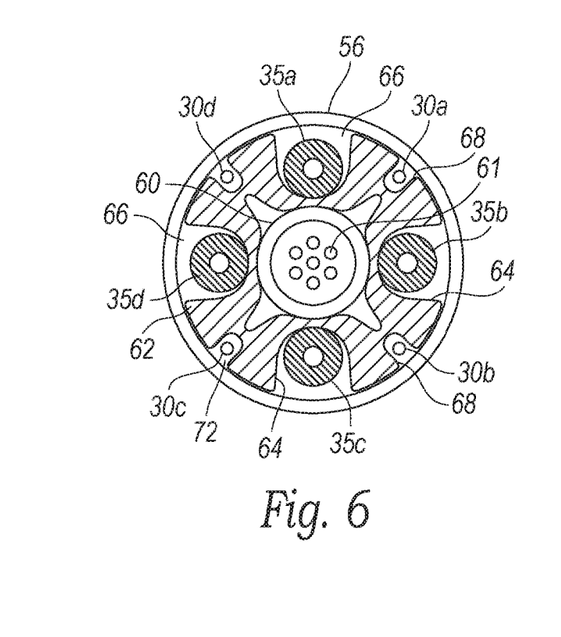
FIG. 6 is a transverse cross-sectional view of the insertion tube of FIG. 5, taken along line 6-6.

Insertion tube 20 also includes one or more distal inertial measurement units (IMUs) 25 disposed at tube distal end 21. IMUs 25 may be incorporated into optical module 22 or mounted separately therefrom, as illustrated in FIG. 2. As shown in FIG. 5 and described below, an intermediate IMU 27 may also be disposed at the proximal end of distal segment 50. An inertial measurement unit is an electronic device that measures and reports an object's specific acceleration, angular rate, and magnetic field surrounding the object, using a combination of accelerometers, gyroscopes, and magnetometers. An IMU works by detecting linear acceleration, rotational rate, and heading reference. When applied to each axis, an IMU can provide pitch, roll, and yaw as well as linear movement. When incorporated into Inertial Navigation Systems, the raw IMU measurement data are utilized to calculate attitude, angular rates, linear velocity and position relative to a global reference frame. IMU data allows a computer to track an object's position, using a method known as dead reckoning or the process of calculating one's current position by using a previously determined position, or fix, and advancing that position based upon known or estimated speeds over elapsed time and course. IMU navigation can suffer accuracy limitations from accumulated error or drift. This error is expected to be reduced in the present technology by combining IMU data with image data generated by optical module 22 such that each subsequent image serves as both a new and a cumulative navigational reference. Associating each image frame or a sampling of image frames with a discrete distal IMU pose data point to create a discrete image pose datum is expected to allow navigation errors to be removed.

Figure 3:
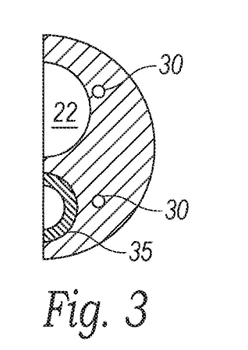
FIG. 3 is a transverse cross-sectional view of the distal portion of the endoscope of FIG. 2, taken along line 3-3.
Figure 4:
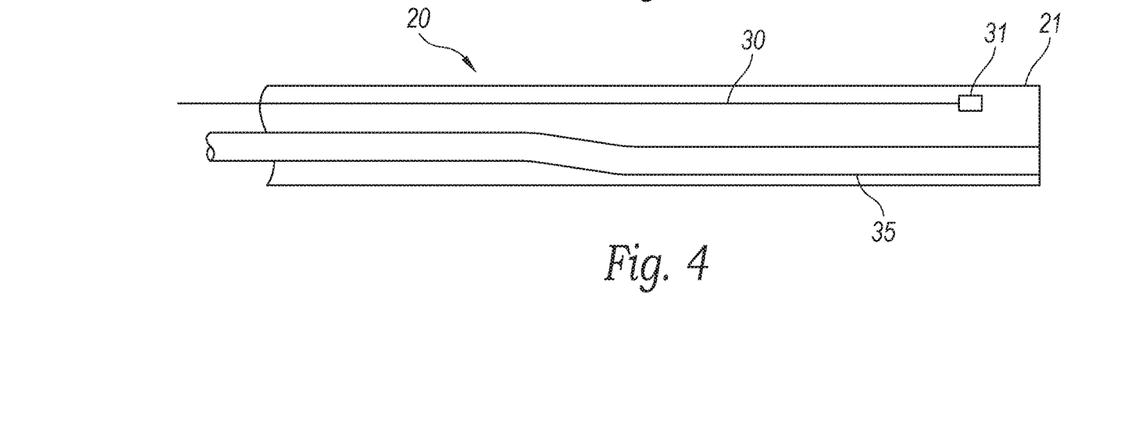
FIG. 4 shows another longitudinal cross-sectional and partially schematic view of a distal portion of an endoscope in accordance with embodiments of the present technology.

As shown in FIGS. 3 and 4, a plurality of control cables 30 extend proximally through insertion tube 20 from corresponding anchor points 31 at insertion tube distal end 21. As will be understood by a person of ordinary skill in the field of endoscopes, cables 30 may be tensioned singly or in various combinations to alter the shape and/or torsional or bending stiffness of insertion tube 20 to facilitate navigating the sometimes-tortuous pathways through the living body. Actuators for applying tension to cables 30 are described below.

Optionally, insertion tube 20 may include one or more working channel(s) 35 therethrough for delivery of fluids or tools as will be understood by a person of ordinary skill in the field of endoscopes.

Figure 7:
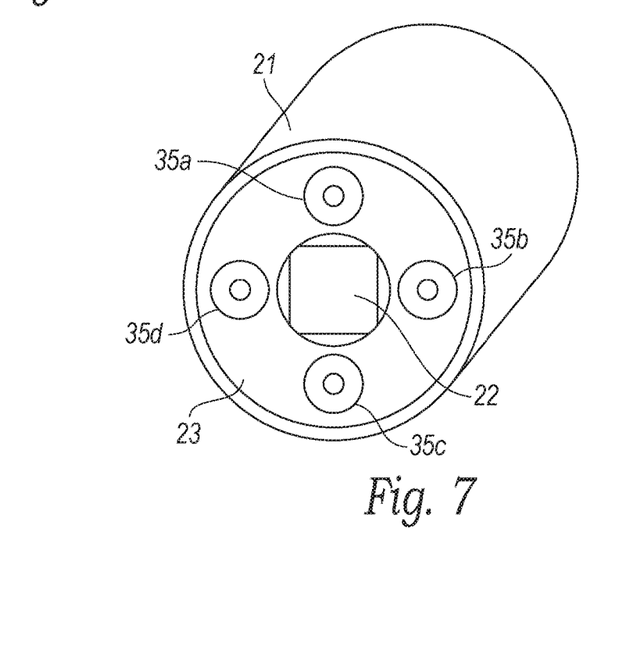
FIG. 7 is an isometric view of the distal end of the insertion tube of FIG. 5.
Figure 8:
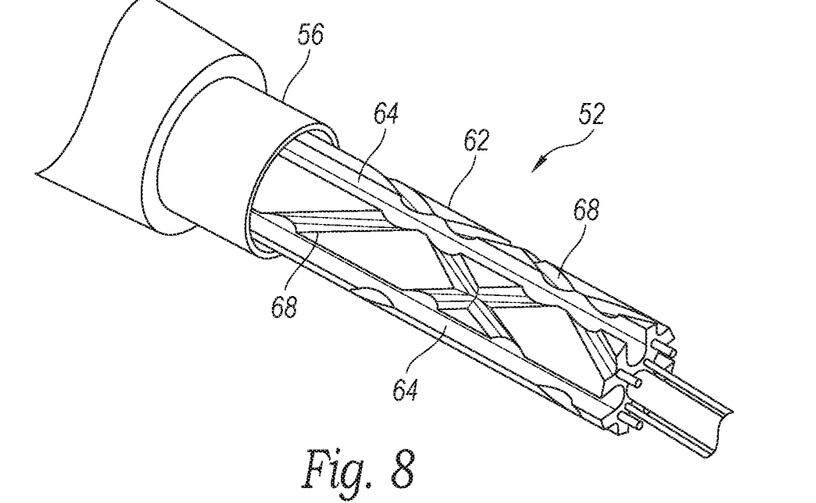
FIG. 8 is a cutaway drawing of the intermediate segment of the insertion tube of FIG. 5. Tubular working channels and control cables are omitted for clarity.

FIGS. 5-9 illustrate another embodiment of an insertion tube 20' in accordance with the present technology. Insertion tube 20' includes, listed from distal end to proximal end, distal tip 21, distal segment 50, intermediate segment 52, strain relief segment 54, and proximal end connector 39. In a flexible endoscope embodiment, distal segment 50 may comprise a bendable active segment, and intermediate segment 52 may be a flexible segment. An outer sheath 56, shown in FIG. 6 but omitted from FIG. 5 for clarity, encloses all the components of insertion tube 20' located distal of connector 39 except for the distal end 23 of insertion tube 20', where optical module 22 is exposed as shown in FIG. 7.

Insertion tube 20' also includes elongate inner tube 60 with electrical wires 61 extending therethrough from connector 39 to, e.g. optical module 22 and IMUs 25, 27. Inner tube 60 is surrounded by elongate spine 62, which has one or more channel grooves 64 configured to receive one or more corresponding tubular working channels 35. See FIGS. 6 and 8. Channel grooves 64 extend longitudinally parallel to a centerline of spine 62 along flexible intermediate segment 52 and bendable active segment 50. In the exemplary embodiment, four working channels 35a-c extend from a side port in connector 39 to insertion tube distal end 23, and are confined to channel lumens 66 defined between channel grooves 64 of spine 62 and outer sheath 56.

Spine 62 has a plurality of cable grooves 68 configured to receive one or more corresponding cables 30. See FIGS. 6 and 8. Cable grooves 68 are helical along flexible intermediate segment 52 and extend longitudinally parallel to a centerline of spine 62 along bendable active segment 50. In the exemplary embodiment, four cables 30 extend from connector 39 to insertion tube distal tip 21, and are confined to cable lumens 72 defined between cable grooves 68 of spine 62 and outer sheath 56. A first and second pair of 180 degree opposed helical cable grooves 68 have reverse chirality or handedness such that the first and second pair of grooves 68 intersect or cross each other repeatedly along flexible intermediate segment 52. For example, cables 30a and 30c extend through respective cable lumens 72 of spine 62 to define a congruent double right-handed helix and cables 30b and 30d extend through respective cable lumens 72 of spine 62 to define a congruent double left-handed helix. Each pair of cable lumens 72, e.g. lumens carrying cables 30a and 30c, remains opposed 180 degrees along flexible intermediate segment 52 and bendable active segment 50 to balance tension forces and to define an orthogonal bending plane within active segment 50. At least at distal end 21, cables 30a and 30c are spaced 90 degrees from cables 30b and 30d to provide at least two orthogonal planes of bending in active segment 50. Since all cable grooves 72 are formed in spine 62 at the same radius from the center of spine 62, cables 30 may have sliding contact with each other where they intersect. Cables 30 extend proximally from corresponding anchor points 31 (see FIG. 4) to connector 39. As shown in FIG. 5, cables 30 are disposed around, i.e. outside of working channels 35. However, it is also an embodiment of the current technology for the spine grooves to be configured such that the working channels 35 are disposed outside of the cables 30.

Figure 9:
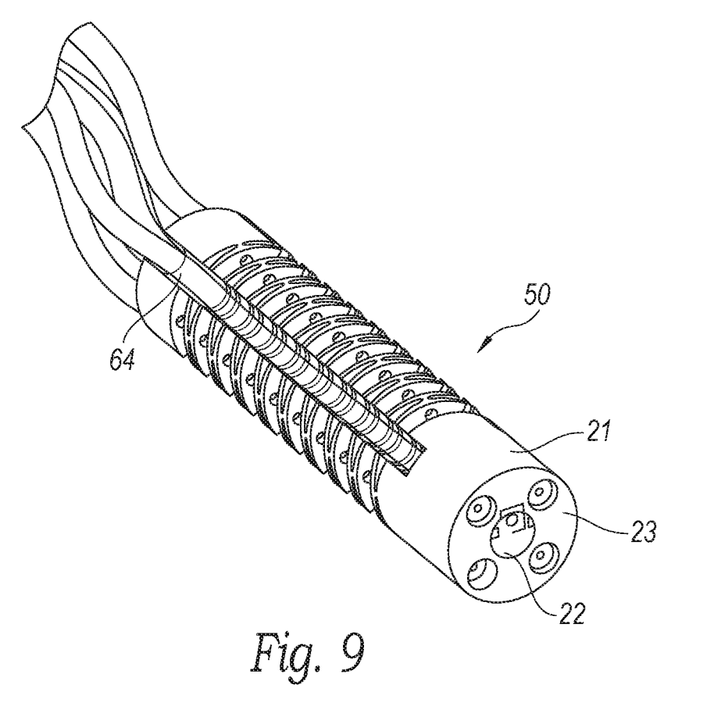
FIG. 9 is an isometric view of the distal end of the insertion tube of FIG. 5. The outer sheath, tubular working channels and control cables are omitted for clarity.

Bendable active segment 50 is configured to be sufficiently flexible to be deflectable in any direction in response to combinations of tensioning in control cables 30, as shown in FIG. 9. Flexible intermediate segment 52 may include intermediate IMU 27 disposed at the distal end thereof, and is less flexible than active segment 50. However, the torsional or bending stiffness of intermediate segment 52 can be controllably increased, for example, by simultaneously tensioning all cables 30. Thus, the torsional or bending stiffness of intermediate segment 52 can be altered regardless of the straight or deflected shape of active segment 50. Conversely, active segment 50 can be controllably deflected independently of the stiffness that may have been induced into intermediate segment 52. Optional strain relief segment 54 may be provided to further increase inherent stiffness and kink-resistance at the proximal end of insertion tube 20'. Strain relief segment 54 may comprise a spiral or helical coil of suitable metal or polymer, and may be disposed either inside or outside of cables 30, and either inside or outside of outer sheath 56. Outer sheath 56 encases all the components of insertion tube 20' as described above to provide a sterility barrier and to provide mechanical properties that contribute significantly to the torsional and/or bending stiffness of insertion tube 20, 20'. For example, outer sheath 56 may provide 20-50% of the overall bending stiffness of fully assembled insertion tube 20.

Figure 1:
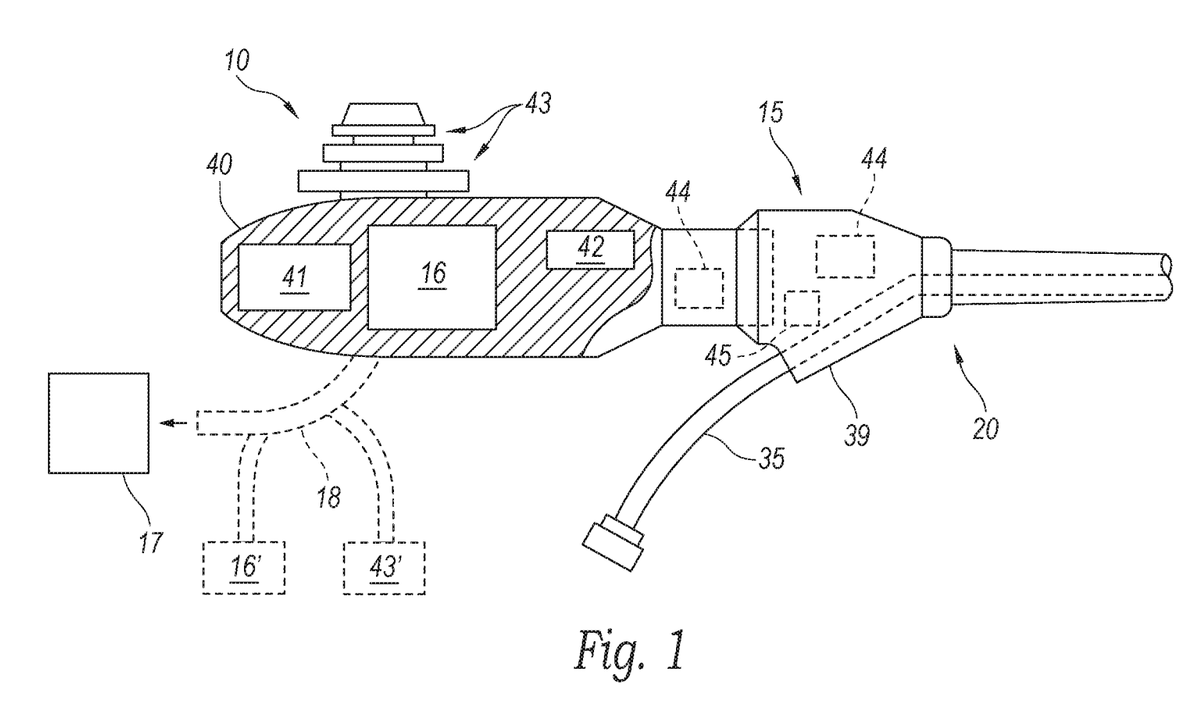
FIG. 1 is a partially schematic view of a proximal portion of an endoscope in accordance with embodiments of the present technology.

Flexible endoscope 15 includes a handle 40 connected to proximal end connector 39 of insertion tube 20. Handle 40 is also connectable to insertion tube 20' or any other interchangeable members of an endoscope family having a common connector 39. One or more proximal IMUs 44 may be disposed in handle 40 and/or in connector 39 at the proximal end of insertion tube 20, as shown in FIGS. 1 and 5. A battery 41 may be mounted in handle 40 as shown. Optionally, electrical power may be provided to endoscope 15 via an electrical cable similar to cable 18. Alternatively, handle 40 is releasably connected to the proximal end of insertion tube 20. The releasable connection may be a quick-release type, such as a quarter-turn fastening or bayonet-type mount and may incorporate facilitated electrical connections for IMUs 25, 27, 44 and optical module 22 as well as facilitated mechanical connections between cables 30 and associated actuators 42.

Handle 40 includes a plurality of actuators 42, each actuator 42 being operatively associated with a corresponding cable extending proximally from insertion tube 20. Actuators 42 may be selected from various types of actuators including linear or rotary, electric (e.g. electro-mechanical), mechanical, hydraulic, pneumatic, twisted and coiled polymer (TCP) or supercoiled polymer (SCP), thermal or magnetic shape memory alloys. A single actuator 42 is shown in FIG. 1 for clarity of illustration, and a connection between actuator 42 and cable 30 is omitted for clarity and because the general concept of actuators and cables will be understood by a person of ordinary skill in the field of endoscopes.

One or more manually operable controllers, i.e. haptic input devices 43 are located on handle 40 for providing force feedback while inputting electronic commands for manipulating endoscope physical properties, i.e. for steering and/or adjusting the torsional and bending stiffness characteristics of insertion tube 20. Haptic input devices 43 may be any suitable type of programmable or pre-programmed kinesthetic or tactile communication devices such as magnetoresistive (MR) controls or motor controllers with feedback. Haptic devices 43 are illustrated as rotary controls that may simulate the steering wheels found on conventional endoscopes. Alternatively, other haptic input devices may be incorporated into handle 40 such as joysticks, touchpads, or keypads, etc. In another alternative embodiment, endoscope system 10 may include haptic input devices 43' located separately from handle 40 as shown in FIG. 1. At the discretion of the clinician, haptic devices 43' may be used to override any communications from haptic devices 43 on handle 40. In yet another alternative embodiment, input devices 43, 43' are not haptic-type devices. Such non-haptic devices can input commands to computer 16 for manipulating endoscope physical properties in situations where force feedback is not required.

Computer 16 is illustrated as being physically mounted in handle 40. Alternatively, computer 16' can be located separately from endoscope 15 on a conventional endoscopy tower or "stack," and can communicate with endoscope 15 via cable or data port 18 as shown in FIG. 1. Computer 16 is configured for converting image data received from optical module 22 into two-dimensional images displayable on monitor 17. In alternative embodiments where endoscope 15 has more than one optical module 22, computer 16 is configured for converting image data received from the plurality of optical modules 22 into three-dimensional images displayable on monitor 17.

Ideal handling characteristics of an endoscope are dependent on the tortuosity of the anatomy. For ideal handling, the rigidity, flexibility and torsional requirements will be different for tighter anatomic turns from the requirements for milder anatomic turns. Computer 16 is configured for steering and/or adjusting torsional and bending stiffness characteristics of insertion tube 20 by driving the plurality of actuators 42 in response to a) one or more command inputs from the one or more haptic input devices 43, and/or b) data from distal IMU(s) 25 and intermediate IMU 27 identifying directional changes as insertion tube distal end 21 is pushed through the anatomy of the living body. Each discrete anatomic bend can be characterized by distal IMU(s) 25 and intermediate IMU 27 according to parameters such as bend length, angle of bend, and distance from prior bend. This data from distal IMU(s) 25 and intermediate IMU 27 can then be used by computer 16 to automatically and dynamically adjust bending stiffness and torsional characteristics to pre-defined specification ranges. During endoscopy, if distal IMU(s) 25 and/or intermediate IMU 27 do not register forward movement of insertion tube distal end 21 despite movement registered in proximal IMU(s) 44, then computer 16 may drive actuators 42 as necessary to adjust the bending stiffness and torsional characteristics of insertion tube 20 to facilitate forward movement of insertion tube distal end 21. Should forward movement of insertion tube distal end 21 be detected by distal IMU(s) 25 and intermediate IMU 27 in response to the adjustments, computer 16 will save data regarding the anatomical bend and bending stiffness/torsional characteristics in a memory function for future algorithm refinement.

Computer 16 is configured for creating a digital three-dimensional anatomy model by combining position and orientation data received from one or more IMUs 25, 27 and/or 44 and image data received from optical module 22. The image data received from optical module 22 comprises a plurality of image frames and the spatial pose data received from distal IMU 25 comprises discrete distal IMU pose data points, as measured by distal IMU 25 and/or intermediate IMU 27, sequentially arranged along a path traced through the living body by the insertion tube distal end 21. Computer 16 creates a digital three-dimensional or spatial image map for an anatomy model by associating each image frame or a sampling of image frames with a discrete distal IMU pose data point to create a discrete image pose datum. Each image pose datum is stored by computer 16 as a) a new reference and b) relative to prior references. As the path is re-traced through the living body by the insertion tube distal end, computer 16 replaces orientation data previously received from distal and proximal IMUs 25, 27 and/or 44 and replaces image data previously received from optical module 22. Computer 16 progressively stitches together each image frame or sampling of image frames from optical module 22 using the associated pose data point from distal IMU 25 to orientate the frames in a set of three-dimensional planes surrounding the path thereby creating a three-dimensional or spatial image map of the anatomy displayable as an endoluminal rendering on monitor 17. Since the rendered image derived from the three-dimensional or spatial image representation contains historical spatial data from distal IMUs 25 associated with each image frame and distal IMU 25 contains the current pose of insertion tube distal end 21 as well as information about the flexing tip of the endoscope, the current pose of insertion tube distal end 21 as well as the flexing tip can be referenced on the three-dimensional or spatial image model in real-time, thus enabling auxiliary portrayals of the anatomy to enable better understanding of the endoscope tip location and orientation. The overall path of the anatomy is discerned from the time series of the IMU poses with the image data surrounding these path points being available for display as needed to enhance understanding of anatomy being explored. Computer 16 can create an external representation of the approximate spatial path of the anatomy that can be shown simultaneously with video images from optical module 22.

If additional data regarding the measured distance from the distal end 21 to the anatomy surface is obtained, then computer 16 may portray the current location and orientation of insertion tube distal end 21 superimposed on an endoluminal rendering of the three-dimensional surface anatomy model on monitor 17. The distance from the distal end 21 to the anatomy surface may be measured by incorporating stereo cameras, a structured-light three-dimensional scanner using projected light patterns, or a time-of-flight range-imaging camera (none of which are shown).

Computer 16 is also configured to provide the one or more manual rotary controls with kinesthetic or haptic communication relative to the tensile load applied by the one or more of the actuators to the corresponding cables. This haptic communication may be driven by computer 16 to emulate the manual feel of operating the steering wheels of a conventional, strictly mechanical endoscope. Emulation may be achieved by computer 16 by reference to a) calibration data for insertion tube 20, and/or b) pre-defined specifications, e.g. a series of pre-defined ratios of kinesthetic or haptic feedback to insertion tube kinematic outputs.

Calibration data may be associated with an individual insertion tube 20, as measured or determined during manufacturing, or calibration data may generally extend to a series or family of identical insertion tubes 20 along with their corresponding flexible tip sections 50. A memory module 45 containing calibration data may optionally be disposed within insertion tube 20, as shown in FIG. 1 as being located near the proximal end of insertion tube 20. For endoscopes 15 where handle 40 is releasably connected to insertion tube 20, computer 16 may set up specific emulation handling parameters based upon the calibration data read from memory module 45 in the connected insertion tube 20. Alternatively, the calibration data could be stored on board the insertion tube 20 as a quick response code (QR code) or similar barcode where the meaning of the code is either known to computer 16 or can be looked up via a network. In such an arrangement, handle 40 may include a suitable code reader adapted to view the QR code before, after, or during the connection of insertion tube 20 and handle 40, i.e. via connector 39.

As an example of a method of determining calibration data for an insertion tube 20, insertion tube 20 is manufactured and placed in a testing rig to determine how many rotations of a haptic rotary input device it takes to achieve flexion and torsion targets. These rotations are saved and stored on memory module 45 in insertion tube 20 and are used to calibrate the number of turns a haptic device 43 on the handpiece must turn in order to move insertion tube 20 to a consistent and predictable position. Thus, calibration data is indicative of the physical properties of an insertion tube 20. For example, if (input of) 2 turns in a manufacturing test rig are required to achieve a 180° bend (output) of insertion tube 20, but a pre-defined usage standard says a 180° bend should only require 1.5 turns, then the calibration data stored in memory module 45 will inform computer 16 to modify command inputs such that each turn of rotary input device 43 by a clinical user would actually make the associated actuator move 1.25 times (2/1.5).

Thus, computer 16 is configured to perform the following steps:
  receive input commands from the one or more haptic rotary input devices 43,
  modify the input commands with reference to the calibration data readable in memory module 45, and
  use the modified input commands to drive the plurality of actuators and thereby operate the corresponding cables to consistently achieve a pre-defined ratio of rotary control rotation inputs to insertion tube kinematic outputs.

In alternative embodiments, the haptic input devices may be other than rotary controllers. In such embodiments, the inputs would involve measures of motion in joysticks, movement of fingers on touchpads, or keyboard entries, etc. In one embodiment, computer 16 can drive the actuators to emulate a pre-defined manual sensation or feel of the device controls rather than, as in the above example, achieve an expected number of rotations to generate a certain bend in insertion tube 20. In this case, computer 16 uses the modified input commands to drive the plurality of actuators and thereby operate the corresponding cables to consistently achieve a pre-defined ratio of kinesthetic haptic feedback to insertion tube kinematic outputs. With the above methods, a semi-robotic endoscope using the present technology can emulate the manual feel of a conventional strictly manual endoscope, thus requiring minimal training of a clinician accustomed to conventional devices.

The computer 16 may comprise a processor and a computer-readable storage medium that stores instructions that when executed by the processor, carry out the functions attributed to the computer 16 as described herein. Although not required, aspects and embodiments of the present technology can be described in the general context of computer-executable instructions, such as routines executed by a general-purpose computer, e.g., a server or personal computer. Those skilled in the relevant art will appreciate that the present technology can be practiced with other computer system configurations, including Internet appliances, hand-held devices, wearable computers, cellular or mobile phones, multi-processor systems, microprocessor-based or programmable consumer electronics, set-top boxes, network PCs, mini-computers, mainframe computers and the like. The present technology can be embodied in a special purpose computer or data processor that is specifically programmed, configured or constructed to perform one or more of the computer-executable instructions explained in detail below. Indeed, the term "computer" (and like terms), as used generally herein, refers to any of the above devices, as well as any data processor or any device capable of communicating with a network, including consumer electronic goods such as game devices, cameras, or other electronic devices having a processor and other components, e.g., network communication circuitry. Data processors include programmable general-purpose or special-purpose microprocessors, programmable controllers, application specific integrated circuits (ASICs), programmable logic devices (PLDs), or the like, or a combination of such devices. Software may be stored in memory, such as random-access memory (RAM), read-only memory (ROM), flash memory, or the like, or a combination of such components. Software may also be stored in one or more storage devices, such as magnetic or optical based disks, flash memory devices, or any other type of non-volatile storage medium or non-transitory medium for data. Software may include one or more program modules which include routines, programs, objects, components, data structures, and so on that perform particular tasks or implement particular abstract data types.

The present technology can also be practiced in distributed computing environments, where tasks or modules are performed by remote processing devices, which are linked through a communications network, such as a Local Area Network ("LAN"), Wide Area Network ("WAN"), or the Internet. In a distributed computing environment, program modules or sub-routines may be located in both local and remote memory storage devices. Aspects of the present technology described herein may be stored or distributed on computer-readable media, including magnetic and optically readable and removable computer discs, stored as in chips (e.g., EEPROM or flash memory chips), etc. Alternatively, aspects of the present technology may be distributed electronically over the Internet or over other networks (including wireless networks). Those skilled in the relevant art will recognize that portions of the present technology may reside on a server computer, while corresponding portions reside on a client computer. Data structures and transmission of data particular to aspects of the present technology are also encompassed within the scope of the present technology.

Examples

Several aspects of the present technology are set forth in the following examples.

1. An endoscope comprising:
a flexible elongate insertion tube having a deflectable distal end, a proximal end connected to a handle, and an intermediate flexible segment therebetween;
an intermediate inertial measurement unit (IMU) disposed at the distal end of the intermediate segment;
an optical module disposed at the insertion tube distal end and adapted to receive images of a body cavity of a living body;
one or more distal IMUs disposed at the insertion tube distal end; and a plurality of cables extending proximally through the insertion tube from corresponding anchor points at the insertion tube distal end;
wherein the handle comprises:
a plurality of actuators, each actuator being operatively associated with a corresponding cable;
one or more haptic input devices for inputting commands for manipulating the physical properties of the insertion tube; and
a computer configured for:
steering and/or adjusting torsional and bending stiffness characteristics of the insertion tube by driving the plurality of actuators in response to one or more command inputs from the one or more haptic input devices;
creating a digital three-dimensional image representation of an anatomy model by combining position and orientation data received from the distal and intermediate IMUs and image data received from the optical module;
converting image data received from the optical module into two-dimensional images displayable on a monitor extrinsic to the endoscope; and
facilitating handling properties of the endoscope by driving the plurality of electro-mechanical actuators to automatically and dynamically adjust torsional and bending stiffness characteristics of the insertion tube to correspond to the tortuosity of the anatomy model.

2. The endoscope of example 1 wherein the image data received from the optical module comprises a plurality of image frames and the position and orientation data received from the distal and intermediate IMUs comprises discrete distal IMU pose data points sequentially arranged along a path traced through the living body by the insertion tube distal end; and
wherein creating a digital three-dimensional spatial image representation further comprises:
associating each image frame or a sampling of image frames with a discrete distal IMU pose data point to create a discrete image pose datum; and
storing each image pose datum as a) a new reference and b) relative to prior references.

3. The endoscope of example 2 wherein creating a digital three-dimensional spatial image representation further comprises, as the path is re-traced through the living body by the insertion tube distal end, replacing pose data previously received from the distal and proximal IMUs and replacing image data previously received from the optical module.

4. The endoscope of example 2 wherein creating a digital three-dimensional spatial image representation further comprises progressively stitching together each image frame or sampling of image frames using the associated pose data point to locate and orientate the frames in a set of three-dimensional planes surrounding the path thereby creating the three-dimensional spatial image representation displayable as an endoluminal rendering on an extrinsic monitor.

5. The endoscope of example 4 wherein the computer is further configured for portraying the current location and orientation of the insertion tube distal end superimposed on an endoluminal rendering of the three-dimensional spatial image representation on an extrinsic monitor.

6. The endoscope of example 1 wherein the insertion tube proximal end is releasably connected to the handle.

7. The endoscope of example 1 wherein the computer is further configured to provide the one or more input devices with kinesthetic haptic feedback relative to the tensile load applied by the one or more of the actuators to the corresponding cables.

8. The endoscope of example 7 wherein the haptic feedback is controlled by the computer to emulate the manual feel of operating a strictly mechanical endoscope.

9. An endoscope system comprising:
an endoscope having:
a flexible elongate insertion tube having a distal end, a proximal end connected to a handle, and an intermediate flexible segment therebetween;
an intermediate inertial measurement unit (IMU) mounted at the distal end of the intermediate segment;
an optical module disposed at the insertion tube distal end and adapted to receive images of a body cavity of a living body;
one or more distal IMUs disposed at the insertion tube distal end; and
a plurality of cables extending proximally through the insertion tube from corresponding anchor points at the insertion tube distal end;
wherein the handle comprises:
a plurality of actuators, each actuator being operatively associated with a corresponding cable;
one or more haptic input devices for inputting commands for manipulating the physical properties of the insertion tube; and
a computer configured for:
steering and/or adjusting torsional and bending stiffness characteristics of the insertion tube by driving the plurality of actuators in response to one or more command inputs from the one or more controls;
creating a digital three-dimensional spatial image representation by combining pose data received from the distal and proximal IMUs and image data received from the optical module;
converting image data received from the optical module into two-dimensional images displayable on a monitor; and
facilitating handling properties of the endoscope by driving the plurality of electro-mechanical actuators to automatically and dynamically adjust torsional and bending stiffness characteristics of the insertion tube to correspond to the tortuosity of the anatomy model in accordance with pre-defined specifications.

10. An endoscope comprising:
a flexible elongate insertion tube having a distal end and a proximal end releasably connected to a handle;
an optical module disposed at the insertion tube distal end and adapted to receive images of an interior of a living body;

a plurality of cables extending proximally through the insertion tube from corresponding anchor points at the insertion tube distal end; and a memory module disposed within the insertion tube and containing calibration data;

wherein the handle comprises:
- a plurality of electro-mechanical actuators, each actuator being operatively associated with a proximal end of a corresponding cable;
- one or more manually operable rotary controllers for inputting commands for manipulating the insertion tube physical properties; and
- a computer configured for:
    - receiving input commands from the one or more controllers;
    - modifying the input commands with reference to the calibration data; and
    - using the modified input commands to drive the plurality of actuators and thereby operating the corresponding cables to consistently achieve a pre-defined ratio of controller rotations to insertion tube kinematic outputs.

11. The endoscope of example 10 wherein the calibration data is indicative of the physical properties of the insertion tube.

12. The endoscope of example 11 wherein the physical properties of the insertion tube are measurable at the time of manufacture.

13. The endoscope of example 10 wherein the pre-defined ratio of controller rotations to insertion tube kinematic outputs emulates the manual feel of operating a strictly mechanical endoscope.

14. An endoscope comprising:

a flexible elongate insertion tube having a distal end and a proximal end releasably connected to a handle;

an optical module disposed at the insertion tube distal end and adapted to receive images of an interior of a living body;

a plurality of cables extending proximally through the insertion tube from corresponding anchor points at the insertion tube distal end; and a means of storing calibration data within the insertion tube;

wherein the handle comprises:
- a plurality of electro-mechanical actuators, each actuator being operatively associated with a proximal end of a corresponding cable;
- one or more haptic input devices for inputting commands for manipulating the insertion tube physical properties; and
- a computer configured for:
    - receiving input commands from the one or more input devices;
    - modifying the input commands with reference to the calibration data; and
    - using the modified input commands to drive the plurality of actuators and thereby operating the corresponding cables to consistently achieve a pre-defined ratio of haptic device kinesthetic feedback to insertion tube kinematic outputs.

15. The endoscope of example 14 wherein the pre-defined ratio of haptic device kinesthetic feedback to insertion tube kinematic outputs emulates the manual feel of operating a strictly mechanical endoscope.

16. A method of using an endoscope, comprising:

inserting an elongate flexible insertion tube into a pathway in a patient's body; and operating one or more input devices disposed on a handle to manipulate physical properties of the insertion tube via a computer.

17. The method of example 16 further comprising receiving force feedback via the one or more input devices regarding the physical properties of the insertion tube and/or contact forces between the insertion tube and the pathway in the patient's body.

18. The method of example 16 further comprising viewing an image on a monitor, the image being created by the computer using data received from an optical module disposed at a distal end of the insertion tube.

19. The method of example 18 wherein, the image on the monitor is a three-dimensional image representation of an anatomy model; and wherein the computer additionally uses position and orientation data received from one or more inertial measurement units (IMUs) disposed in the insertion tube to create the image.

20. A computer-readable storage medium storing instructions that, when executed by a computing system, cause the computing system to perform operations for performing a method of operation in an endoscopic system, the instructions comprising:

receiving position and orientation data from a distal inertial measurement unit (IMU) positioned at a deflectable distal end portion of an endoscope;

receiving position and orientation data from an intermediate IMU positioned at an intermediate flexible portion of the endoscope; and based on the position and orientation data from the distal and intermediate IMUs, driving a plurality of electro-mechanical actuators of the endoscope to dynamically adjust torsional and/or bending stiffness characteristics of the deflectable distal end portion and/or the intermediate flexible portion of the endoscope.

21. The computer-readable storage medium of example 20 wherein the instructions further comprise:

generating a digital three-dimensional image representation of an anatomy model by combining the position and orientation data received from the distal and intermediate IMUs; and wherein driving the plurality of electro-mechanical actuators of the endoscope includes driving the plurality of electro-mechanical actuators to dynamically adjust torsional and/or bending stiffness characteristics of the deflectable distal end portion and/or the intermediate flexible portion of the endoscope to correspond to a tortuosity of the anatomy model.

22. The computer-readable storage medium of example 20 wherein the instructions further comprise:

receiving image data of a body cavity of a living body from an optical module positioned at the deflectable distal end portion of the endoscope; and converting the image data received from the optical module into two-dimensional images displayable on a monitor.

23. The computer-readable storage medium of example 22 wherein the instructions further comprise creating a digital three-dimensional image representation of the body cavity by combining (a) the position and orientation data received from the distal and intermediate IMUs and (b) the image data received from the optical module.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An endoscope system comprising:
    a flexible elongate insertion tube having a deflectable distal end and a proximal end releasably connected to a handle;
    an optical module disposed at the distal end of the insertion tube and adapted to receive images of a body cavity of a living body;
    one or more distal inertial measurement units (IMUs) disposed at the distal end of the insertion tube;
    one or more intermediate IMUs disposed at a proximal end of a distal segment of the insertion tube, the distal segment proximally extending from the distal end of the insertion tube; and
    a plurality of cables extending proximally through the insertion tube from corresponding anchor points at the distal end of the insertion tube;
    wherein the handle comprises:
        a plurality of electro-mechanical actuators, each actuator being operatively associated with a corresponding cable extending through the insertion tube;
        one or more haptic devices for inputting commands for manipulating physical properties of the insertion tube; and
        a computer configured for:
            manipulating physical properties of the insertion tube by driving the plurality of electro-mechanical actuators in response to one or more command inputs from the one or more haptic devices;
            creating a digital three-dimensional image representation of an anatomy model by combining position and orientation data received from the one or more distal IMUs and intermediate IMUs, and image data received from the optical module;
            facilitating handling properties of the insertion tube by driving the plurality of electro-mechanical actuators to dynamically and automatically adjust torsional and bending stiffness characteristics of the insertion tube to pre-defined specification ranges which correspond to a tortuosity of the anatomy model; and
            converting the image data received from the optical module into two-dimensional images displayable on a monitor extrinsic to the handle,
        wherein dynamic and automatic adjustment of the electro-mechanical actuators via the computer is achieved as a response to the position and orientation data received from the one or more distal IMUS and intermediate IMUS, the position and orientation data including bend length, angle of bend, and distance from prior bend.

2. The endoscope system of claim 1, wherein the plurality of electro-mechanical actuators are operable robotically via a data port on the handle.

3. The endoscope system of claim 1, wherein the computer is further configured to provide the one or more haptic devices with kinesthetic haptic feedback relative to a tensile load applied by the plurality of electro-mechanical actuators to the corresponding cables.

4. The endoscope system of claim 3, wherein the haptic feedback is controlled by the computer to emulate the manual feel of operating a strictly mechanical endoscope.

5. The endoscope system of claim 1, wherein the computer is further configured to drive the plurality of electro-mechanical actuators in response to the one or more command inputs from the one or more haptic devices to achieve a pre-defined ratio of measured haptic device input motions to insertion tube kinematic outputs.

6. The endoscope system of claim 5, wherein the one or more haptic devices are rotary controllers; and
    wherein a pre-defined ratio of controller rotations to the insertion tube kinematic outputs emulates the manual feel of operating a strictly mechanical endoscope.

7. The endoscope system of claim 5, further comprising a memory module disposed within the insertion tube and containing calibration data; and
    wherein the computer is further configured to modify the one or more command inputs with reference to the calibration data before driving the plurality of electro-mechanical actuators.

8. The endoscope system of claim 1, further comprising:
    one or more proximal IMUs disposed in the handle and/or in a connector at the proximal end of the insertion tube; and
    wherein the computer is further configured to combine the position and orientation data received from the one or more distal, intermediate, and/or proximal IMUs into the creation of the digital three-dimensional image representation of the anatomy model.

9. The endoscope system of claim 1, wherein the image data received from the optical module comprises a plurality of image frames and wherein the position and orientation data received from the one or more distal and/or intermediate IMUs comprises discrete IMU pose data points sequentially arranged along a path traced through the living body by the distal end of the insertion tube; and wherein the computer is further configured to create the digital three-dimensional image representation by:
associating each image frame or a sampling of image frames with a discrete IMU pose data point to create a discrete image pose datum; and
storing each image pose datum as a) a new reference and b) relative to prior references.

10. The endoscope system of claim 9, wherein the computer is further configured to create the digital three-dimensional image representation by, as the path is re-traced through the living body by the distal end of the insertion tube, replacing pose data previously received from the distal IMUs and replacing the image data previously received from the optical module.

11. The endoscope system of claim 9, wherein the computer is further configured to create the digital three-dimensional image representation by progressively stitching together each image frame or sampling of image frames using the associated pose data point to locate and orientate the frames in a set of three-dimensional planes surrounding the path thereby creating the three-dimensional image representation displayable as an endoluminal rendering on the monitor extrinsic to the handle.

12. The endoscope system of claim 9, wherein the computer is further configured for portraying a current location and orientation of the distal end of the insertion tube superimposed on an endoluminal rendering of the three-dimensional image representation on the monitor extrinsic to the handle.

13. An endoscope system comprising:
an elongate insertion tube having a distal end and a proximal end releasably connected to a handle;
one or more optical modules disposed at the distal end of the insertion tube and adapted to receive images of a body cavity of a living body;
one or more distal inertial measurement units (IMUs) disposed in the insertion tube distal end;
one or more intermediate IMUs disposed at a proximal end of a distal segment of the insertion tube, the distal segment proximally extending from the distal end of the insertion tube; and
a computer configured for:
combining position and orientation data received from the one or more distal IMUs and intermediate IMUs, and image data received from the optical module to create a digital three-dimensional image representation of an anatomy model displayable on a monitor extrinsic to the handle; and
facilitating handling properties of the insertion tube by driving a plurality of electro-mechanical actuators to dynamically and automatically adjust torsional and bending stiffness characteristics of the insertion tube to pre-defined specification ranges which correspond to a tortuosity of the anatomy model,
wherein dynamic and automatic adjustment of the electro-mechanical actuators via the computer is achieved as a response to the position and orientation data received from the one or more distal IMUs and intermediate IMUs, the position and orientation data including bend length, angle of bend, and distance from prior bend.

14. The endoscope system of claim 13, wherein the computer is further configured for converting the image data received from the optical module into two-dimensional images displayable on the monitor extrinsic to the handle.

15. The endoscope system of claim 13 further comprising:
one or more proximal IMUs disposed in the handle and/or in a connector at the proximal end of the insertion tube; and
wherein the computer is further configured to combine position and orientation data received from the proximal IMUs into the creation of the digital three-dimensional image representation of the anatomy model.

16. The endoscope system of claim 13, wherein the image data received from the optical module comprises a plurality of image frames and wherein the position and orientation data received from the distal IMUs and the intermediate IMUs comprises discrete IMU pose data points sequentially arranged along a path traced through the living body by the distal end of the insertion tube; and
wherein the computer is further configured to create the digital three-dimensional image representation by:
associating each image frame or a sampling of image frames with a discrete IMU pose data point to create a discrete image pose datum; and
storing each image pose datum as a) a new reference and b) relative to prior references.

17. The endoscope system of claim 16, wherein the computer is further configured to create the digital three-dimensional image representation by, as the path is re-traced through the living body by the distal end of the insertion tube, replacing pose data previously received from the IMUs and replacing the image data previously received from the optical module.

18. The endoscope system of claim 16, wherein the computer is further configured to create the digital three-dimensional image representation by progressively stitching together each image frame or sampling of image frames using the associated pose data point to locate and orientate the frames in a set of three-dimensional planes surrounding the path thereby creating the three-dimensional image representation displayable as an endoluminal rendering on the monitor extrinsic to the handle.

19. The endoscope system of claim 16, wherein the computer is further configured for portraying a current location and orientation of the distal end of the insertion tube superimposed on an endoluminal rendering of the three-dimensional image representation on the monitor extrinsic to the handle.

20. The endoscope system of claim 13, wherein the computer is disposed in the handle.

21. The endoscope system of claim 13, wherein the computer is disposed extrinsic to the handle.

22. An endoscope system comprising:
a flexible elongate insertion tube having a deflectable distal end and a proximal end releasably connected to a handle;
an optical module disposed at the distal end of the insertion tube and adapted to receive images of a body cavity of a living body;
one or more distal inertial measurement units (IMUs) disposed at the distal end of the insertion tube;
one or more intermediate IMUs disposed at the proximal end of the distal segment of the insertion tube, the distal segment proximally extending from the distal end of the insertion tube; and
a plurality of cables extending proximally through the insertion tube from corresponding anchor points at the distal end of the insertion tube;
wherein the handle comprises:
a plurality of electro-mechanical actuators, each actuator being operatively associated with a corresponding cable extending through the insertion tube;

one or more haptic devices for inputting commands for manipulating physical properties of the insertion tube; and a computer configured for facilitating handling properties of the endoscope by driving the plurality of electro-mechanical actuators to automatically and dynamically adjust torsional and bending stiffness characteristics of the insertion tube as a response to position and orientation data received from the one or more distal IMUs and intermediate IMUs, the position and orientation data including bend length, angle of bend, and distance from prior bend.

\* \* \* \* \*